United States Patent [19]
Miyata et al.

[11] Patent Number: 5,314,874
[45] Date of Patent: May 24, 1994

[54] INTRACORPOREALLY INJECTABLE COMPOSITION FOR IMPLANTING HIGHLY CONCENTRATED CROSS-LINKED ATELOCOLLAGEN

[75] Inventors: Teruo Miyata; Tadatomo Kawai, both of Tokyo, Japan

[73] Assignee: Koken Co., Ltd., Tokyo, Japan

[21] Appl. No.: 872,722

[22] Filed: Apr. 15, 1992

[30] Foreign Application Priority Data

Apr. 19, 1991 [JP] Japan .................................. 3-113660

[51] Int. Cl.$^5$ ...................... A61L 33/00; C08B 37/10; C07K 15/20; A61K 7/12
[52] U.S. Cl. ........................................ 514/21; 530/356
[58] Field of Search ........................... 514/21; 530/356

[56] References Cited

U.S. PATENT DOCUMENTS

| | | | |
|---|---|---|---|
| 4,242,291 | 12/1980 | Hughes et al. | 264/1 |
| 4,424,208 | 1/1984 | Wallace et al. | 427/177 |
| 4,582,640 | 4/1986 | Smestad et al. | 530/356 |
| 4,803,075 | 2/1989 | Wallace et al. | 424/423 |
| 4,837,285 | 6/1989 | Berg et al. | 530/356 |
| 5,080,670 | 2/1992 | Imamura et al. | 623/2 |

FOREIGN PATENT DOCUMENTS

| | | |
|---|---|---|
| 89145 | 9/1983 | European Pat. Off. . |
| 0132979 | 2/1985 | European Pat. Off. . |
| 196197 | 3/1985 | European Pat. Off. . |
| 0212933 | 3/1987 | European Pat. Off. . |
| 268421 | 5/1988 | European Pat. Off. . |
| 0330389 | 8/1989 | European Pat. Off. . |
| WO9012055 | 10/1990 | European Pat. Off. . |
| 0411124 | 2/1991 | European Pat. Off. . |
| 62-26230 | 6/1987 | Japan . |

*Primary Examiner*—Howard E. Schain
*Assistant Examiner*—P. Lynn Touzeau
*Attorney, Agent, or Firm*—Varndell Legal Group

[57] ABSTRACT

The present invention provides an intracorporeally injectable non-toxic composition of atelocollagen having an excellent, long-lasting skin swelling effect due to its low viscosity, good fluidity, easy injectability and low antigenicity (without calcification) properties. The composition is prepared by treating an aqueous suspension of atelocollagen with a buffer for physiological conditions. The suspension can have atelocollagen content of 55 to 75 mg/ml, where approximately 20 to 100% by weight of atelocollagen is cross-linked with a polyepoxy compound.

6 Claims, 4 Drawing Sheets

INTRACORPOREALLY INJECTABLE COMPOSITION FOR IMPLANTING HIGHLY CONCENTRATED CROSS-LINKED ATELOCOLLAGEN

BACKGROUND OF THE INVENTION

The present invention relates to an aqueous suspension of collagen which is formed by a cross-linking reaction using a cross-linking agent, such as a polyepoxy compound. The cross-linked collagen is intracorporeally injectable and useful as repair material for soft tissue depression deficiency.

Collagen is a protein richly distributed in skin, cornea, vessels, sinew, bones and the like of animals. It is a sticky molecule with a molecular weight of about 0.3 million and has a helical structure consisting of three polypeptide chains with a molecular length of approximately 300 nm and a diameter of approximately 1.5 nm.

A bundle of five collagen molecules is called a microfibril and forms a structure separated by only 67 nm from the adjacent molecule. A microfibril has a thickness of about 4 nm and is the fundamental structural unit of collagen fiber. Many microfibrils comprise a fibril, and a bundle of fibrils comprises a collagen fiber. Sinew or the like is tissue in which the collagen fibers are arranged in an orderly fashion while skin is a tissue made up of entangled collagen fibers.

Fibrous collagen exhibits cross-linking between the molecule, and this cross-linking generally exists in the telopeptide showing no triple helix present at the terminal point of the collagen molecule. Atelocollagen can be obtained by digesting the telopeptide moiety with an enzyme such as pepsin. Since the main antigen determining group of collagen exists in the telopeptide moiety, the atelocollagen in which this telopeptide moiety has been digested hardly shows antigenicity and is therefore useful as medical material.

This atelocollagen is useful for repairing tissue deficient regions of soft tissues like skin by injecting an aqueous suspension of the atelocollagen into the depressed deficient wound, thereby eliminating the need for a surgical operation. The higher the collagen concentration of an aqueous collagen suspension during injection, the more effective the repairing effect is, due to the attendant skin swelling effect. It is preferable from the wound curing and cosmetic point of view to inject a small amount of such an aqueous suspension of atelocollagen at several sites rather than to inject a large amount thereof at one site. Therefore, it is necessary to use a thin needle, such as 27 G or 30 G. As such, a low viscosity is needed for injecting an aqueous suspension of atelocollagen. Thus, the intracorporeally injectable aqueous suspension of atelocollagen should have a high concentration and a low viscosity.

Three types of intracorporeally injectable collagen are proposed. For simplicity, they are referred to below as Collagen A, Collagen B and Collagen C. Collagen A is an aqueous neutral solution of collagen (JP Patent Publication No. Sho 62-37020). Collagen B is an aqueous suspension of collagen fibers, and Collagen C is an aqueous suspension of atelocollagen cross-linked with glutaraldehyde (JP Patent Publication No. Hei 1-36840).

The aqueous neutral solution type Collagen A is viscous at low temperatures. Implantation of this type of collagen into a living body induces the formation of collagen fibers by body temperature, whereby the same collagen structure as living collagen is constituted. Decomposition and absorption of this type of collagen within living bodies occurs slowly and produces a high skin swelling effect. However, it is difficult to inject a highly concentrated solution of Collagen A because of its high viscosity. Injection of a large amount of a highly concentrated solution at one site would form a collagen structure which would tend to prevent the live self-organizing cells from penetrating therein.

An aqueous suspension of collagen fibers (Collagen B) is prepared by subjecting collagen molecules to conditions similar to those of living bodies and dispersing the resulting fibers in water. Since it is difficult to inject the material using a fine needle as is, the fibrous structure must be converted into a very fine structure, in order to allow easy injection. Once the collagen is implanted into a living body, it diffuses below the skin soon after injection, and decomposition and absorption take place quickly. Thus, the skin swelling effect is so low that injection would have to be repeatedly performed to retain the desired result. Certain suspensions of highly concentrated collagen have been developed for overcoming this defect, but the diffusion, decomposition and absorption of such suspensions in a living body occur so rapidly that marked improvement of the skin via the swelling effect has not been observed.

In the case of Collagen B materials, which are not cross-linked, 2 to 3% of persons have been found to be reactive, even though the telopeptide, the main antigenicity-determining group, has been removed. Repeated administration of Collagen B would also likely produce new reactions in 2 to 3% of the previous non-reactive persons. This, of course is a major problem.

Atelocollagen cross-linked with glutaraldehyde (Collagen C) was developed to try to improve the aforesaid problem. Collagen C is an aqueous suspension of a new material prepared by cross-linking atelocollagen with glutaraldehyde, which raises resistance to intracorporeal decomposition and absorption while further lowering antigenicity. However, when atelocollagen is cross-linked with glutaraldehyde, it becomes water-repellent and its fluidity in aqueous suspensions is inferior to that of atelocollagen which is not cross-linked. In particular, the fluidity of a high concentration of Collagen C makes it difficult to inject. As for intracorporeal change of the implanted material with the passage of time, calcification and the like are often observed, together with low identification into self-tissue. This tendency is pronounced at high concentrations. Therefore, it is not appropriate to inject a high concentration of such cross-linked atelocollagen because the skin swelling effect in such a case would only be improved somewhat when compared with that of atelocollagen not cross-linked. The use of glutaraldehyde as a cross-linking agent also poses a problem because of its cytotoxicity.

SUMMARY OF THE INVENTION

In view of the problems above, it is an objective of the present invention to provide an intracorporeally injectable non-toxic composition of cross-linked atelocollagen with low antigenicity and excellent long lasting action of skin-swelling effect without inducing calcification, and which is easily injectable with good fluidity at low viscosity even when used in high concentrations.

As the result of various investigations concerning cross-linking agents of atelocollagen suitable for intracorporeal injection to attain the objectives above, the present inventors have found that the polyepoxy compounds are very appropriate as cross-linking agents, and the present invention has been established.

Accordingly, the present invention relates to a composition containing 55 to 75 mg/ml of atelocollagen wherein approximately 20 to 100% by weight of the atelocollagen has been cross-linked with a polyepoxy compound. The composition is preferably used in the implantation of aqueous suspensions of atelocollagen that have been adjusted for physiological conditions with a buffer.

DESCRIPTION OF THE PREFERRED EMBODIMENTS

Figure 1:
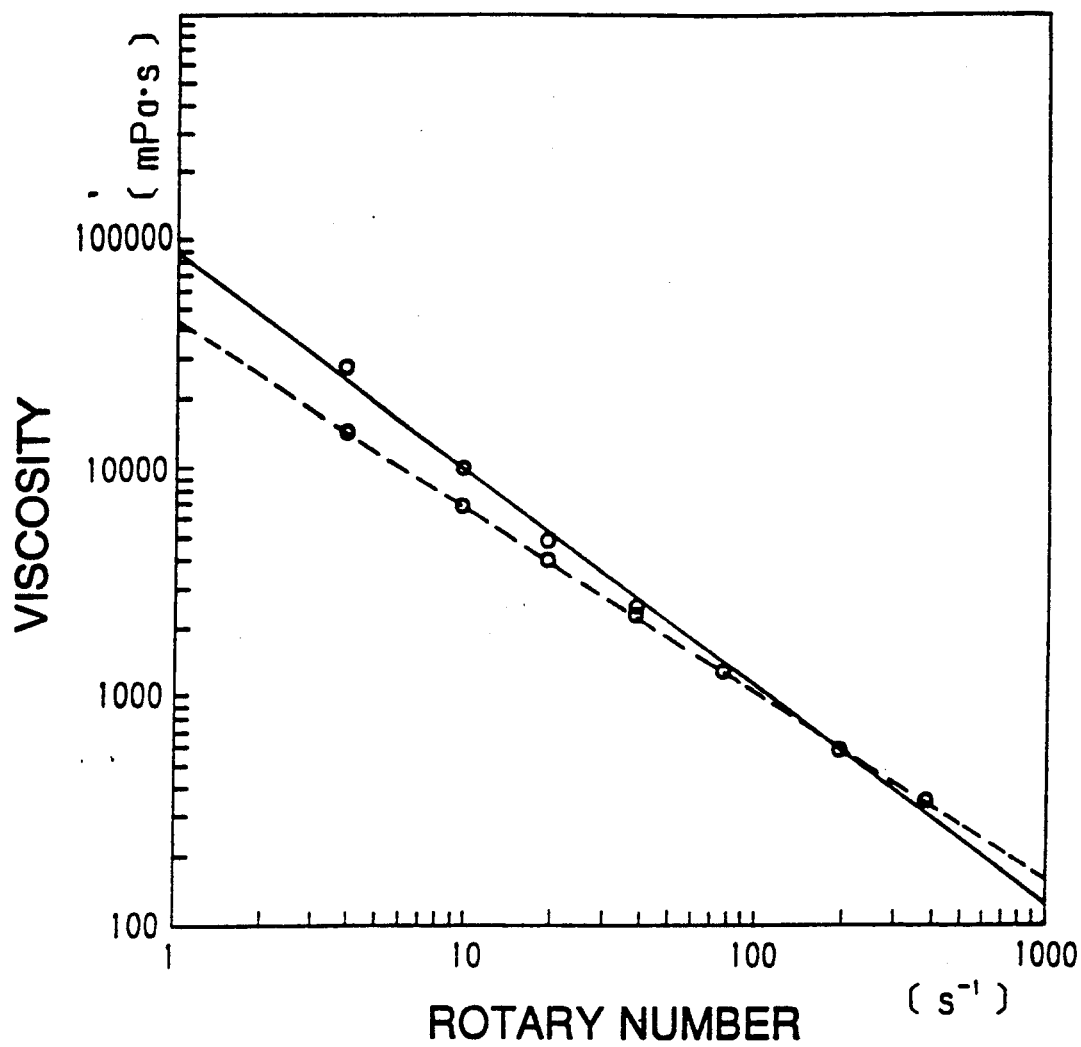
FIG. 1 is a plot of viscosity versus rotary number and shows the viscoelasticity performance of atelocollagen cross-linked with a 3.5% (by weight) polyepoxy compound.

The atelocollagen usable in the present invention is a collagen extractible by reacting connective tissue of various animals with an enzyme such as pepsin or the like to cut the cross-linkage between the collagen molecules for solubilization. Since the telopeptide, the main antigenicity determining group, is removed during solubilization with an enzyme, the donor of atelocollagen need not be an inheritably identical strain with its receptor. The atelocollagen is ordinarily prepared by solubilizing bovine dermis with pepsin because of easy availability.

Polyepoxy compounds suitable as cross-linking agents in the present invention include hydrophilic polyepoxy compounds, polyether polyol derivatives are preferred. For example, the polyepoxy compounds can include glycerol diglycidyl ether, glycerol triglycidyl ether, diglycerol tetraglycidyl ether, triglycerol pentaglycidyl ether, poly (methylene glycol) diglycidyl ether (1-10 polymerization degree), poly (ethylene glycol) diglycidyl ether (1-10 polymerization degree), poly (trimethylene glycol) diglycidyl ether (1-8 polymerization degree), poly (propylene glycol) diglycidyl ether (1-8 polymerization degree) and the like.

The cross-linking reaction with these cross-linking agents may be generally performed in the aqueous phase at temperature from 20° to 37° C. for 0.5 to 72 hours. The aqueous phase includes distilled water, water treated with hydrochloric acid or sodium hydroxide for changing the pH, water buffered with phosphate buffer, borate buffer, carbonate buffer or the like, without particular limitation.

An appropriate application rate of the polyepoxy compound is 0.1 mg to 2 g per 1 g of atelocollagen. Appropriate concentration of atelocollagen in the reaction mixture is 0.1 to 5% by weight. The reaction is carried out over a period of prescribed time, and the cross-linked reaction mixture is recovered. The cross-linking reaction is allowed to stop by adding an amino group-containing reagent such as glycine, ethanolamine or the like to the mixture. After washing sufficiently, the mixture is concentrated to a concentration of 6 to 10% by weight of atelocollagen.

The concentrated mixture is adjusted to physiological conditions with a phosphate buffer to a concentration of atelocollagen of 55 to 75 mg/ml (5.5 to 7.5% by weight). Thus, the objective of the invention—to form an intracorporeally injectable composition for implanting highly concentrated cross-linked atelocollagen—can be obtained.

All the atelocollagen molecules in the atelocollagen solution are cross-linked to produce a cross-linked atelocollagen using the process described above. Thus, there can be obtained a product in which 100% by weight of atelocollagen has been cross-linked with a polyepoxy compound. All the atelocollagen molecules cross-linked with a polyepoxy compound are usable in the composition for implantation of the present invention. There are also usable compositions in which not less than 20% by weight, preferably not less than 40% by weight, of atelocollagen has been cross-linked with a polyepoxy compound. For example, such a composition may be prepared by adding atelocollagen to the atelocollagen solution cross-linked as above until the content of cross-linked atelocollagen reaches a prescribed amount. If the content of cross-linked atelocollagen is less than 20% by weight, decomposition and absorption within the living body cannot be inhibited sufficiently, and the swelling effect by injection into the depressed form deficient region of the soft tissue cannot be maintained over a long period of time.

In the cross-linked atelocollagen of the present invention, more than 10%, preferably more than 20%, most preferably more than 40%, of the amino side chain groups of the atelocollagen molecules have been reacted with a polyepoxy compound. The effect due to the cross-linking reaction is not observed on the cross-linked atelocollagen in which less than 10% of the amino groups have been reacted with a polyepoxy compound. In such a case, decomposition and absorption of the atelocollagen with the living body cannot be inhibited sufficiently.

An aqueous suspension of the atelocollagen cross-linked with a polyepoxy compound in the present invention shows a specific performance of very low viscosity which is different from aqueous suspensions of atelocollagen cross-linked with other cross-linking agents at the same concentration. For example, a 3.5% (by weight) aqueous suspension of atelocollagen cross-linked with glutaraldehyde shows 5000 m Pa·s corresponds to a shearing stress of 100 s$^{-1}$ rotary number when the viscoelasticity is measured with a rotational viscometer. However, a 3.5% (by weight) aqueous suspension of the atelocollagen cross-linked with a polyepoxy compound shows a lower viscosity performance of 900 m Pa·s in case of a shearing stress of 100 s$^{-1}$ rotary number, and a 6% (by weight) aqueous suspension of the atelocollagen cross-linked with a polyepoxy compound shows 5000 m Pa·s in case of a shearing stress of 100 s$^{-1}$ rotary number.

In this way, an aqueous suspension of atelocollagen cross-linked with a polyepoxy compound in the present invention shows advantageously low viscosity and good fluidity even at a high concentration, enabling facilitation of smooth intracorporeal injection. Thus, intracorporeal injection can be effected at a high concentration of 55 to 75 mg/ml in the present invention. As intracorporeal injection is effected at such a higher concentration, the skin swelling effect becomes more pronounced. At a concentration of less than 55 mg/ml, the skin swelling effect and its retaining effect, namely volume retaining effect, are not sufficient. When the concentration is in excess of 75 mg/ml, the aqueous suspension of atelocollagen cross-linked with a polyepoxy compound cannot be easily injected because of high viscosity and low fluidity.

The cross-linked atelocollagen of the present invention shows a transition temperature (temperature to transfer into gelatin) of not less than 40° C. when measured with a differential scanning calorimeter. It exhibits an especially preferable transition temperature of 50° to 80° C. When the transition temperature is less than 40° C., the decomposition and absorption of atelocollagen within a living body is sufficiently inhibited because of an insufficient degree of cross-linkage.

The aqueous suspension of atelocollagen cross-linked with a polyepoxy compound in the present invention provides numerous advantages over the prior art. Among these advantages are: (1) less toxicity in comparison to atelocollagen cross-linked with other cross-linked agents such as glutaraldehyde, (2) low antigenicity without calcification with little histinonic reaction, and (3) facilitated invasion of fibroblast and identification into self-tissue with rapid achievement of the skin swelling effect. Thus, it is appropriate to inject the atelocollagen suspension of the invention into depressed or void regions of soft tissue wounds caused by traffic accidents, operations, injuries or the like. Further, other additives such as local anesthetics or the like may be added thereto, if necessary.

Presently preferred and practical embodiments of the present invention will be illustratively shown in the following example.

EXAMPLE 1

Fresh bovine dorsal skin was cut off, and its periphery ripped away. The dorsal skin was washed with city water to remove stains attached on the outside of the skin and then washed with water free of pyrogen. The skin thus obtained was dipped in 70% ethanol, and the hair and the upper side of the skin was scraped with a razor to remove the hairy root. At this time, it is necessary to ensure that the surface of the dermis remains free from dirt.

The back side of the skin was also scraped with a razor, and only the dermis layer of bovine skin was removed so that it might not be stained. The removed dermis layer was dipped overnight in 70% alcohol, the excess alcohol was removed, and the dermis layer was sterilizedly pulverized. Then, the pulverized dermis was washed with 5% brine free of pyrogen, centrifuged for dehydration, washed with pyrogen free water, and dipped in 70% alcohol overnight. After removing the excess alcohol by centrifugation, the pulverized dermis was put in a sterilized dissolving tank, mixed with pyrogen-free water, and a solution of pepsin dissolved in pyrogen-free water which was freed from germs by filtration. In this case, the amount of pepsin added to the pulverized dermis was 0.5% (based on dry weight). The concentration of dermis was kept at about 0.5 to 0.9% by weight, the pH was adjusted to 3 with hydrochloric acid, and the temperature was kept at 20° C. The resulting mixture was stirred at 20° C. intermittently for 3 days to completely dissolve the insoluble dermis collagen, whereby an atelocollagen solution was obtained.

The aqueous solution (pH 3) of atelocollagen coming from bovine dermis solubilized with pepsin was successively filtered through filters of 1 μm, 0.80 μm, 0.65 μm and 0.45 μm pore diameter in that order, but twice in the filter of 0.45 μm pore diameter. This solution was adjusted to pH 7 with sterile 0.5N sodium hydroxide for fiber formation, and a 2% aqueous solution of atelocollagen was prepared with distilled water free of pyrogen (2 stage distillation). The solution was adjusted to pH 9 with 0.04 M $Na_2PO_4$ and 0.3M brine, stirred at 35° C. for 5 hours while warming and mixed with ethylene glycol diglycidyl ether to a final concentration of 0.5%. The reaction mixture was stirred for 15 hours, and after the reaction was completed, the dispersion was recovered by centrifuge.

The resulting product was dispersed in distilled water (2 stage distillation) to a 2% concentration of collagen, mixed with 0.04M $Na_2PO_4$, 0.3M NaCl and 0.4M aqueous glycine solution to a 1% concentration of collagen, and then stirred at 35° C. for 15 hours to inactivate the remaining epoxy group. The product was recovered by centrifuge and washed well with 0.02M $Na_2HPO_4$ and 0.15M NaCl aqueous solution in order to produce an aqueous suspension of atelocollagen cross-linked with a polyepoxy compound of 6% (by weight) of collagen (60 mg/ml). The ε-amino group modifying rate of this cross-linked atelocollagen was 49.2% as the result of examination according to the TNBS method, and the analysis with a differential scanning calorimeter showed a transition temperature of 60.1° C.

EXAMPLE 2

Following the same procedures utilized in Example 1, a 3.5 wt. % aqueous suspension of atelocollagen cross-linked with a polepoxy compound (ethylene glycol diglycidyl ether) was prepared. The ε-amino group modifying rate was 49.2%.

EXAMPLE 3

Following the procedures in Example 1, but substituting glutaraldehyde in place of the ethylene glycol diglycidyl ether as a cross-linking agent, a 3.5 wt. % aqueous suspension of atelocollagen cross-linked with glutaraldehyde was prepared. The ε-amino group modifying rate of this cross-linked collagen was approximately 49.2% according to the same analysis as in Example 1.

Measurement of Viscoelasticity

Figure 2:
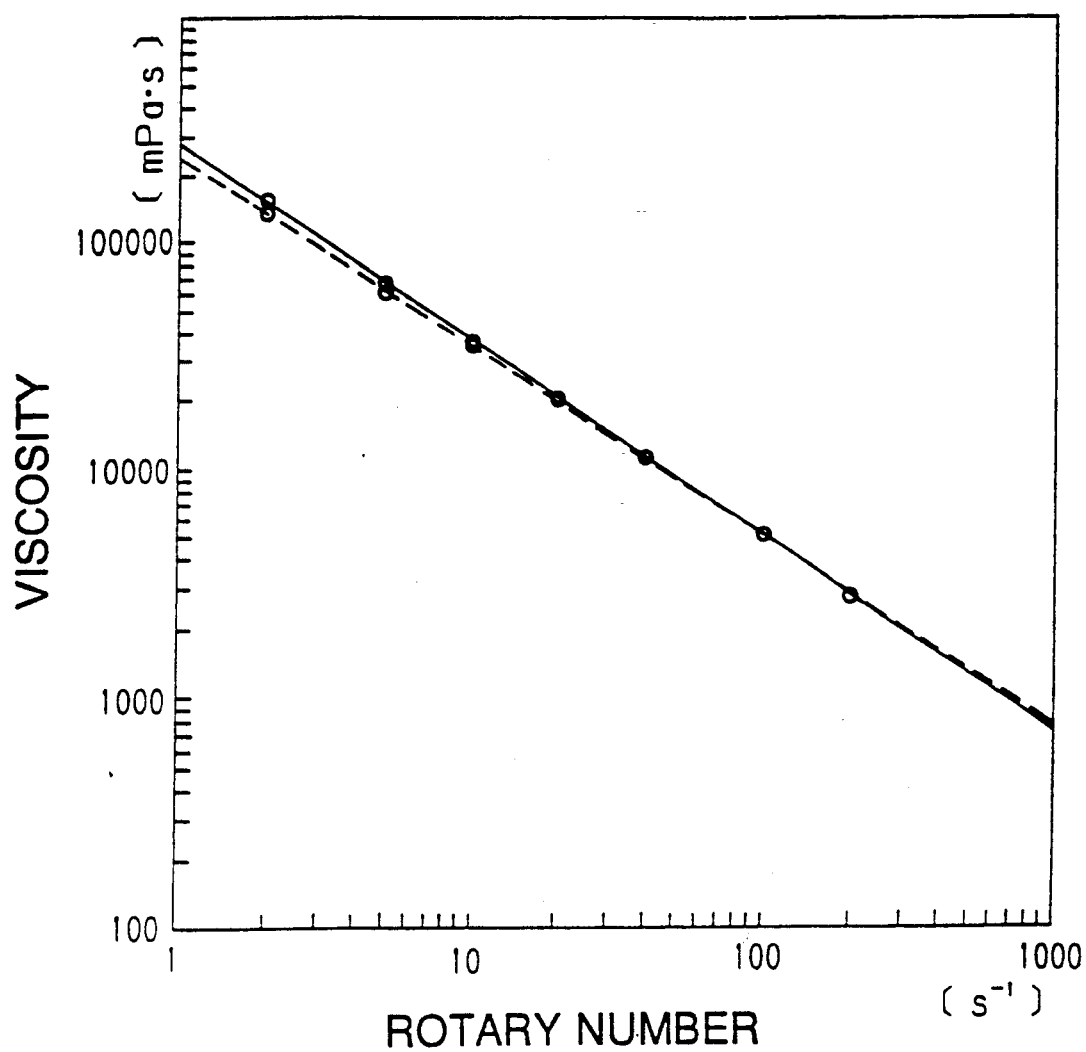
FIG. 2 is a plot of viscosity versus rotary number and shows the viscoelasticity performance of atelocollagen cross-linked with a 6% (by weight) polyepoxy compound.
Figure 3:
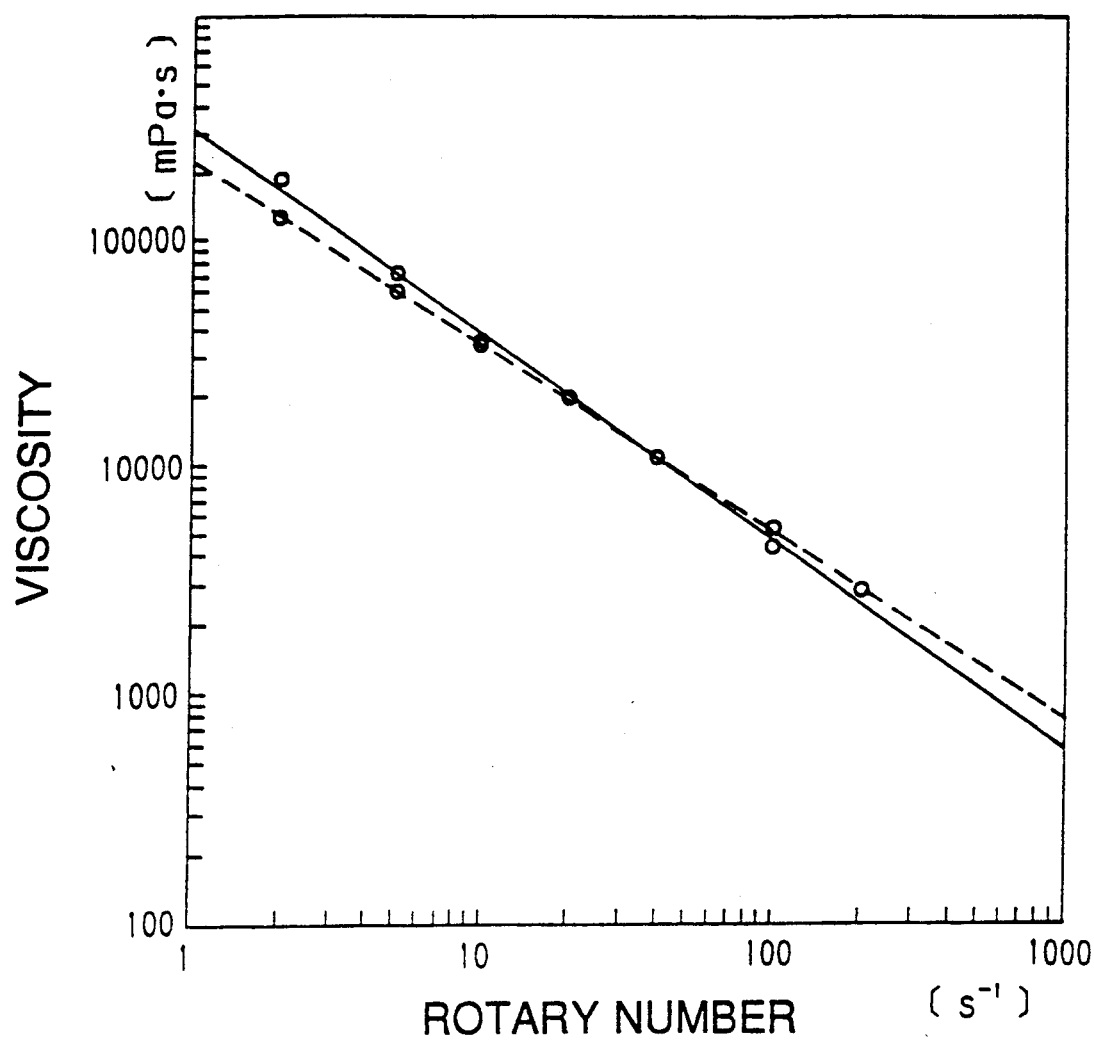
FIG. 3 is a plot of viscosity versus rotary number and shows the viscoelasticity performance of atelocollagen cross-linked with a 3.5% (by weight) glutaraldehyde mixture.

Viscoelasticity was measured with a Corn Plate Type E Rotational Viscometer manufactured by Tokyo Meter. FIGS. 1, 2 and 3 show the results. FIG. 1 shows that the viscoelasticity of the 3.5% by weight (35 mg/ml) aqueous suspension of atelocollagen cross-linked with ethylene glycol diglycidyl ether of Example 2 has a low viscosity performance of 900 m Pa·s corresponding to a shearing stress of 100 $s^{-1}$ rotary number. In FIG. 1, the x-axis is the rotary number, and the y-axis is the viscosity. The solid line demonstrates the results when the rotary number was allowed to increase. The broken line demonstrates the results when the rotary number was allowed to decrease.

FIG. 2 shows a viscosity performance of 5000 m Pa·s corresponding to a shearing stress of 100 $s^{-1}$ rotary number of the 6% by weight (60 mg/ml) aqueous suspension of atelocollagen cross-linked with ethylene glycol diglycidyl ether of Example 1. In FIG. 2, the x-axis is the rotary number, and y-axis is the viscosity. The solid line demonstrates the results obtained when the rotary number was allowed to increase. The broken line demonstrates the results obtained when the rotary number was allowed to decrease.

FIG. 3 shows that the viscoelasticity performance of the 3.5% by weight (35 mg/ml) aqueous suspension of atelocollagen cross-linked with glutaraldehyde of Example 3 is 5000 m Pa·s corresponding to a shearing stress of 100 s$^{-1}$ rotary number. In FIG. 3, the x-axis is the rotary number, and the y-axis is the viscosity. The solid line demonstrates the results obtained when the rotary number was allowed to increase. The broken line demonstrates the results obtained when the rotary number was allowed to decrease.

FIGS. 1-3 demonstrate that an aqueous suspension of atelocollagen cross-linked with a polyepoxy compound in accordance with the present invention shows a very low viscosity, in contrast to atelocollagen cross-linked with other cross-linking agents, such as glutaraldehyde.

EXAMPLE 4

In vitro Experiment

Figure 4:
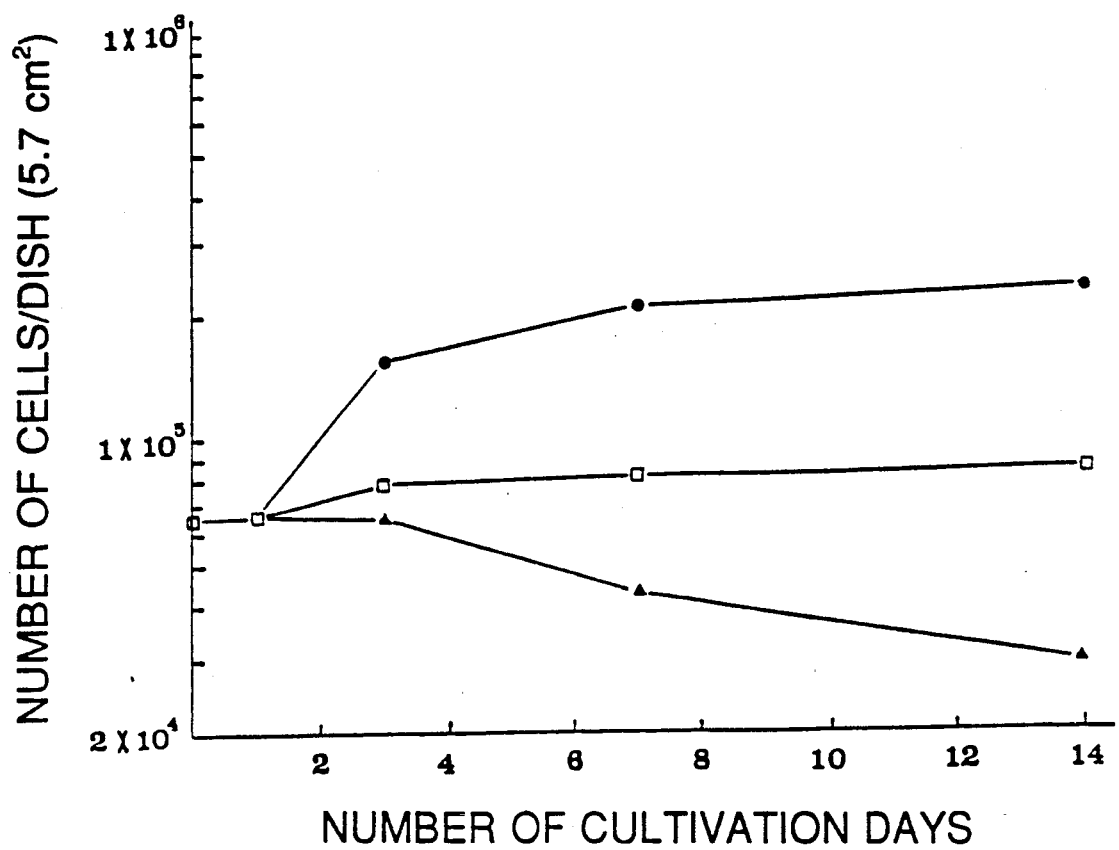
FIG. 4 shows the result of cell growth cultivation on atelocollagen cross-linked with a polyepoxy compound.

Cell growth of collagen cross-linked with a polyepoxy compound was examined according to a cultivation test with human fibroblasts. A culture dish was coated with collagen cross-linked with the polyepoxy compound prepared according to Examples 1 and 2, and dried in air. This was inoculated with 6.5×10$^4$ cells on the culture dish and cultivated at 37° C. using a CO$_2$ incubator. For comparison, cultivation was carried out under similar conditions with non-cross-linked collagen and collagen cross-linked with glutaraldehyde prepared according to Example 3. The results are shown in FIG. 4. In FIG. 4 solid black circular spots show the results of the atelocollagen cross-linked with a polyepoxy compound, the white square spots show the results of the uncross-linked atelocollagen, and the solid black triangle spots show the results of the atelocollagen cross-linked with glutaraldehyde. Also in FIG. 4, the x-axis shows the number of cultivation days, while the y-axis shows the number of cells per dish within an area of 5.7 cm$^2$. In the dish treated with atelocollagen cross-linked with said polyepoxy compound, the cells grew favorable and had a normal shape. On the other hand, significantly less or no cell growth was observed in the dishes treated with the uncross-linked the atelocollagen or atelocollagen treated with glutaraldehyde.

EXAMPLE 5

In vivo Examination

Two male SD rats 4 weeks old were subcutaneously injected with 0.3 ml of 6% by weight (60 mg/ml) aqueous suspension of atelocollagen cross-linked with a polyepoxy compound (prepared according to Example 1) through the dorsal skin. A biopsy was performed at every prescribed time period as set forth in Tables 1 and 2, and a histological examination was made. The results are shown in Table 1.

Table 2 shows the result of 0.3 ml of 3.5% by weight (35 mg/ml) aqueous suspension of atelocollagen cross-linked with a polyepoxy compound (prepared according to Example 2) for comparison. In each table, (−) means no admission or a slight amount of admission, (±) means normal or ordinary admission, (+) means a significant amount of admission, (++) means a large admission, and (+++) means a vigorous or very large admission. Tables 1 and 2 demonstrate that the higher the concentration of aqueous suspension of atelocollagen cross-linked with a polyepoxy compound, the more effective is the volume retaining effect.

TABLE 1

|   | 7 days following implantation | 20 days following implantation | 40 days following implantation | 100 days following implantation |
|---|---|---|---|---|
| invasion of lymphocytes | (+) | (−) | (−) | (−) |
| invasion of phagocytes | (±) | (+) | (+) | (+) |
| foreign body giant cells | (−) | (+) | (++) | (+) |
| vascularization | (±) | (++) | (+) | (+) |
| fibroblast | (±) | (++) | (+++) | (++) |
| newly produced collagen from rats | (−) | (++) | (+++) | (++) |
| calcicosis | (−) | (−) | (−) | (−) |
| volume retaining effect | (+++) | (+++) | (+++) | (++) |

TABLE 2

|   | 7 days following implantation | 20 days following implantation | 40 days following implantation | 100 days following implantation |
|---|---|---|---|---|
| invasion of lymphocytes | (+) | (−) | (−) | (−) |
| invasion of phagocytes | (±) | (+) | (+) | (+) |
| foreign body giant cells | (−) | (+) | (++) | (+) |
| vascularization | (±) | (++) | (+) | (+) |
| fibroblast | (±) | (++) | (+++) | (++) |
| newly produced collagen from rats | (−) | (++) | (+++) | (++) |
| calcicosis | (−) | (−) | (−) | (−) |
| volume retaining effect | (+++) | (++) | (++) | (++) |

In the present invention, since the intracorporeally injectable composition of atelocollagen cross-linked with a polyepoxy compound as a cross-linking agent controls the intracorporeal absorption of atelocollagen, the atelocollagen composition is characterized by low viscosity and good fluidity even at a high concentration. This facilitates intracorporeal injection, enabling the swelling effect to be maintained over a long period of time. The present invention of intracorporeally injectable composition of cross-linked atelocollagen confers a number of benefits, since it shows no toxicity, low antigenicity, no calcification, little historic reaction, and the dermal swelling effect can be attained together with rapid invasion of fibroblast and assimilation into self tissue.

What is claimed is:

1. A composition comprising an aqueous suspension of atelocollagen adjusted for physiological conditions by a buffer to a concentration of 55 to 75 mg/ml of said atelocollagen, wherein said atelocollagen is cross-linked with a polyepoxy compound in an amount of 20 to 100% by weight and not less than 10% of amino side chain groups of atelocollagen contained in said cross-linked atelocollagen are cross-linked with said polyepoxy compound, said polyepoxy compound is a member selected from the group consisting of glycerol diglycidyl ether, glycerol triglycidyl ether, diglycerol tetraglycidyl ether, triglycerol pentaglycidy ether, poly (methylene glycol) diglycidyl ether (1-10 polymerization degree), poly (ethylene glycol) diglycidyl ether (1-10 polymerization degree), poly (trimethylene glycol) diglycidyl ether (1-8 polymerization degree) and poly (propylene glycol) diglycidyl ether (1-8 polymerization degree), said cross-linked atelocollagen has a transition point of not less than 40° C. as measured by a differential scanning calorimeter, and said composition has a viscosity sufficient for injection through a needle.

2. The composition of claim 1, wherein said cross-linked atelocollagen is cross-linked in an amount not less than 40% by weight.

3. The composition of claim 1, wherein said cross-linked atelocollagen is cross-linked in an amount not less than 40% by weight.

4. The composition of claim 1, wherein said cross-linked atelocollagen is cross-linked in an amount not less than 40% by weight.

5. The composition of claim 1, wherein said polyepoxy compound is ethylene glycol diglycidyl ether.

6. The composition of claim 1, wherein a 60 mg/ml atelocollagen suspension of said composition has a viscosity of 5000 m Pa·s at a shearing stress of 100 s$^{-1}$ rotary number.

* * * * *